United States Patent
Hart et al.

(10) Patent No.: US 11,333,650 B2
(45) Date of Patent: *May 17, 2022

(54) DETERMINATION OF ASPHALTENE INHIBITOR PROPERTIES AND TREATMENT OF CRUDE OIL WITH ASPHALTENE INHIBITORS

(71) Applicant: Clariant International, Ltd., Muttenz (CH)

(72) Inventors: Paul R Hart, League City, TX (US); Abhishek Punase, Spring, TX (US); Rama Rao Alapati, Tuttle, OK (US)

(73) Assignee: Clariant International Ltd., Muttenz (CH)

( * ) Notice: Subject to any disclaimer, the term of this patent is extended or adjusted under 35 U.S.C. 154(b) by 86 days.

This patent is subject to a terminal disclaimer.

(21) Appl. No.: 16/573,489

(22) Filed: Sep. 17, 2019

(65) Prior Publication Data

US 2021/0080444 A1 Mar. 18, 2021

(51) Int. Cl.
*G01N 33/28* (2006.01)

(52) U.S. Cl.
CPC ..... *G01N 33/2823* (2013.01); *G01N 33/2835* (2013.01)

(58) Field of Classification Search
CPC .. G01N 33/2823; G01N 27/221; G01N 27/22; G01N 33/2835
USPC .......................................... 73/61.41; 324/686
See application file for complete search history.

(56) References Cited

U.S. PATENT DOCUMENTS

| | | | | |
|---|---|---|---|---|
| 5,420,040 | A | * 5/1995 | Anfindsen | G01N 33/2823 436/60 |
| 10,648,939 | B2 | * 5/2020 | Hascakir | G01N 27/22 |
| 2011/0251795 | A1 | 10/2011 | Difoggio | |
| 2021/0080444 | A1 | 3/2021 | Hart | |
| 2021/0080445 | A1 | 3/2021 | Hart | |

OTHER PUBLICATIONS

Extended European Search Report for EP19215222, dated Jul. 10, 2020, 7 pages.
Punase, A., Mazzeo, C., Garan, R., Vita, E., Kristensen, R., Wylde, J., "Novel In-Field Technique to Monitor and Optimize Asphaltene Remediation and Inhibition Job with Direct Field-to-Laboratory Correlation," 2019, Offshore Technology Conference Brasil, Oct. 25-27, Rio de Janeiro, Brazil, 13 pages.
Aguiar, J., Punase, A., Mazzeo, C., "Influence of Asphaltene Inhibitors on Wax and Asphaltene Deposition—Are Problems Related?" 2019 Offshore Technology Conference Brasil, Oct. 25-27, Rio de Janeiro, Brazil, 14 pages.
Punase, A., Aguiar, J., Smith, R., Mazzeo, C., Wylde, J., "Importance of Comprehending Waxphaltenes and the Need to Develop New inhibitors to Prevent its Deposition" SPE/IATMI Asia Pacific Oil and Gas Conference and Exhibition, Oct. 25-27, 2019, Bali, Indonesia, 10 pages.
Punase, A., Mazzeo, C., Hart, P., Mahmoudkhani, A., Wylde, J. ,"A Novel Thermo-Electric Technique to Evaluate Asphaltene Stability and Inhibitor Efficiency in Native Crude Oil Medium," Offshore Technology Conference, May 6-9, 2019, Houston, Texas, 10 pages.
Punase, A., Aguiar, J., Mahmoudkhani, A., "Impact of Inorganic Salts and Minerals on Asphaltene Stability and Inhibitor Performance," SPE International Conference on Oilfield Chemistry, Apr. 8-9, 2019, Galveston, Texas, 11 pages.
Prakoso, A., Punase, A., Rogel, E., Ovalles, C., Hascakir, B., "Effect of Asphaltene Characteristics on its Solubility and Overall Stability", Energy and Fuels, 2018, 32(06), 6482-6487.
Prakoso, A., Punase, A., Hascakir, B., "A Mechanistic Understanding of Asphaltene Precipitation from Varying Saturate Concentration Perspective", SPE Production & Operations, 2017, 32(01), 86-98, SPE-177280-PA.
Punase, A., Hascakir, B., "Stability Determination of Asphaltenes through Dielectric Constant Measurements of Polar Oil Fractions", Energy and Fuels, 2017, 31(1), 65-77.
Aguiar, J., Mazzeo, C., Garan, R., Punase, A., Razavi, S., Mahmoudkhani, A., "What can we Learn from Analysis of Field Asphaltenes Deposits? Enhancing Product Development through Knowledge Based Field-to-Lab-to-Field Approach," SPE International Conference on Oilfield Chemistry, Apr. 8-9, 2019, Galveston, Texas, 16 pages.

* cited by examiner

*Primary Examiner* — John Fitzgerald
*Assistant Examiner* — Jean F Morello
(74) *Attorney, Agent, or Firm* — Tod A. Waldrop

(57) ABSTRACT

This disclosure relates methods and systems for determining asphaltene inhibitor properties. For example, one embodiment provides a method for determining a content of disaggregated asphaltene in an inhibited crude oil. The method includes measuring the dielectric constant of a sample of the crude oil, the sample having a first concentration of an asphaltene inhibitor; providing a first dielectric correction factor for the first concentration of the asphaltene inhibitor; calculating, e.g., by a computing device, a first corrected dielectric constant of the sample having the first concentration, using the first dielectric correction factor; and determining the content of disaggregated asphaltene in the first crude oil sample, based on the first corrected dielectric constant. Methods for inhibiting asphaltene aggregation in crude oil are also provided.

20 Claims, No Drawings

DETERMINATION OF ASPHALTENE INHIBITOR PROPERTIES AND TREATMENT OF CRUDE OIL WITH ASPHALTENE INHIBITORS

BACKGROUND OF THE INVENTION

This disclosure relates generally to methods and systems for determining properties of asphaltene inhibitors and crude oils inhibited therewith. More particularly, the present disclosure relates to methods for determining degree of asphaltene inhibition in crude oil and methods for determining an inhibition capacity of an asphaltene inhibitor, and the use of such methods to inhibit a crude oil (e.g., in a crude oil matrix).

TECHNICAL BACKGROUND

An asphaltene is not a particular compound, but rather a crude oil solubility class including components that are filterable after dilution in an aliphatic hydrocarbon medium and which subsequently dissolve in an aromatic hydrocarbon medium. Specific hydrocarbon media, dilution/solvation ratio, and filter pore size affect the asphaltene composition obtained from a given sample, but such parameters are not codified in the definition of "asphaltenes." In crude oil production, "asphaltenes" refer generally to the deposits formed when pressure in a production line drops, or when black oil is comingled with gas condensate. In crude oil refining, "asphaltenes" refer generally to the deposits formed when the crude oil is heated or comingled with aliphatic naphtha.

Asphaltene inhibitors, i.e., compounds capable of disaggregating asphaltenes in a crude oil medium, are used to minimize or prevent such deposits. Conventionally, the effectiveness of an asphaltene inhibitor is determined through a sedimentation test, which artificially forces the precipitation of asphaltenes with ten-fold quantities of alkane solvent. Because sedimentation tests necessarily alter the composition of an oil, test results can be unreliable for predicting inhibitor performance in a specific crude oil composition, such as a native crude oil matrix containing produced brine (as is often the case in oil production), which interferes significantly with sedimentation tests.

Accordingly, there remains a need for methods and systems that determine asphaltene inhibitor properties in crude oils, including those in native crude oil matrices and in matrices comprising water.

SUMMARY OF THE DISCLOSURE

One aspect of the disclosure is a method for determining a content of disaggregated asphaltene in an inhibited crude oil, the method including
  measuring the dielectric constant of a sample of the crude oil, the sample having a first concentration of an asphaltene inhibitor;
  providing a first dielectric correction factor for the first concentration of the asphaltene inhibitor;
  calculating, e.g., by a computing device, a first corrected dielectric constant of the sample having the first concentration, using the first dielectric correction factor; and
  determining the content of disaggregated asphaltene in the first crude oil sample, based on the first corrected dielectric constant.

Another embodiment of the disclosure is a method for determining an asphaltene inhibition capacity of an asphaltene inhibitor for a crude oil, the method including
  measuring the dielectric constant of a first sample of the crude oil, the first sample having a first concentration of an asphaltene inhibitor;
  providing a first dielectric correction factor for the first concentration of the asphaltene inhibitor;
  calculating, e.g., by a computing device, a first corrected dielectric constant of the first sample having the first concentration, using the first dielectric correction factor;
  measuring the dielectric constant of a second sample of the crude oil, the second sample having a second concentration of the asphaltene inhibitor;
  providing a second dielectric correction factor for the second concentration of the asphaltene inhibitor;
  calculating, e.g., by the computing device, a second corrected dielectric constant of the sample having the second concentration, using the second dielectric correction factor; and
  determining the asphaltene inhibition capacity of the asphaltene inhibitor, based on the second corrected dielectric constant and the first corrected dielectric constant.

Another aspect of the disclosure is method for selecting one or more target asphaltene inhibitors for a crude oil, comprising
  providing a plurality of asphaltene inhibitors;
  for each inhibitor of the plurality, determining an asphaltene inhibition capacity for the crude oil according as described herein;
  selecting, from the plurality, inhibitors having an asphaltene inhibition capacity above a predetermined cutoff, to provide one or more target asphaltene inhibitors for the crude oil.

Another aspect of the disclosure is a method for determining an effective (e.g., a minimum effective) asphaltene inhibitor concentration for a crude oil, comprising
  measuring the dielectric constant of a first sample of the crude oil, the first sample having a first concentration of an asphaltene inhibitor;
  providing a first dielectric correction factor for the first concentration of the asphaltene inhibitor;
  calculating, e.g., by a computing device, a first corrected dielectric constant of the sample having the first concentration, using the first dielectric correction factor;
  measuring the dielectric constant of the crude oil sample, the sample having a second concentration of the asphaltene inhibitor;
  providing a second dielectric correction factor for the second concentration of the asphaltene inhibitor;
  calculating, e.g., by the computing device, a second corrected dielectric constant of the sample having the second concentration, using the second dielectric correction factor;
  calculating, e.g., by the computing device, based on the first corrected dielectric constant and the second corrected dielectric constant, an effective concentration (e.g., a minimum effective concentration) of the asphaltene inhibitor sufficient to provide
    a predetermined minimum corrected dielectric constant; or
    a predetermined minimum net increase in corrected dielectric constant.

Another aspect of the disclosure is a method for inhibiting a crude oil (e.g., from a crude oil matrix), comprising
   determining an effective (e.g., a minimum effective) asphaltene inhibitor concentration for the crude oil as described herein; and
   adding an amount of the asphaltene inhibitor to the crude oil (e.g., to the crude oil matrix) sufficient to provide an inhibitor concentration of at least the effective asphaltene inhibitor concentration (e.g., at least the minimum effective asphaltene inhibitor concentration).

Another aspect of the disclosure is a method for inhibiting a crude oil (e.g., in a crude oil matrix), comprising
   selecting one or more target asphaltene inhibitors for the crude oil matrix as described herein; and
   adding an amount of a target asphaltene inhibitor to the crude oil (e.g., to the crude oil matrix).

Another aspect of the disclosure is a non-transitory computer-readable medium having stored thereon program instructions that when executed by a processor of a computing device, cause the computing device to perform a set of functions comprising:
   receiving a first dielectric constant of a first sample of a crude oil, the sample having a first concentration of an asphaltene inhibitor;
   calculating a first corrected dielectric constant of the first sample having the first concentration, using a first dielectric correction factor;
   receiving a second dielectric constant of a second sample of the crude oil, the second sample having a second concentration of the asphaltene inhibitor;
   calculating a second corrected dielectric constant of the sample having the second concentration, using a second dielectric correction factor.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Additionally, any enumeration of elements, blocks, or steps in this specification or the claims is for purpose of clarity. Thus, such enumeration should not be interpreted to require or imply that these elements, blocks, or steps adhere to a particular arrangement or are carried out in a particular order.

Regardless of how they may be implemented, the embodiments herein may make use of one or more computing devices. These computing devices may include, for example, client devices under the control of users, and server devices that directly or indirectly interact with the client devices. Such devices are described below.

Various functional components can be included in a computing device arranged to carry out one or more of the embodiments described herein. An example computing device could be a client device, a server device, or some other type of computational platform. Such computing devices can alternatively be provided as hand-held devices configured for use in the field; such devices need not have connectivity to any other device. For purpose of simplicity, this specification may equate a computing device to a server from time to time. Nonetheless, the description of the computing device could apply to any component used for the purposes described herein.

In this example, the computing device includes a processor, a data storage, a network interface, and an input/output function, all of which may be coupled by a system bus or a similar mechanism. The processor can include one or more CPUs, such as one or more general purpose processors and/or one or more dedicated processors (e.g., application specific integrated circuits (ASICs), digital signal processors (DSPs), network processors, etc.).

The data storage, in turn, may comprise volatile and/or non-volatile data storage and can be integrated in whole or in part with the processor. The data storage can hold program instructions, executable by the processor, and data that may be manipulated by these instructions to carry out the various methods, processes, or operations described herein. Alternatively, these methods, processes, or operations can be defined by hardware, firmware, and/or any combination of hardware, firmware and software. By way of example, the data in the data storage may contain program instructions stored on a non-transitory, computer-readable medium, executable by the processor to carry out any of the methods, processes, or operations disclosed in this specification.

The network interface may take the form of a wireline connection, such as an Ethernet, Token Ring, or T-carrier connection. The network interface may also take the form of a wireless connection, such as IEEE 802.11 (Wfi), BLUETOOTH®, or a wide-area wireless connection. However, other forms of physical layer connections and other types of standard or proprietary communication protocols may be used over the network interface. Furthermore, the network interface may comprise multiple physical interfaces.

The input/output function may facilitate user interaction with the example computing device. The input/output function may comprise multiple types of input devices, such as a keyboard, a mouse, a touch screen, and so on. In certain embodiments, the input/output function may comprise a measurement input device, e.g., a dielectric constant measurement device. The input/output function may comprise multiple types of output devices, such as a screen, monitor, printer, or one or more light emitting diodes (LEDs). Additionally or alternatively, the example computing device may support remote access from another device, via the network interface or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

The disclosure relates to methods and systems for determining properties of asphaltene inhibitors and crude oils inhibited therewith. The disclosure demonstrates that such methods and systems are effective for crude oils, including those in native crude oil matrices and in matrices comprising water.

As used herein, the term "crude oil" includes naturally occurring crude oil (i.e., a native crude oil matrix) and crude oil components (e.g., a refined product). A "native crude oil matrix" may include oil production byproducts, e.g., produced brine. As used herein, the term "asphaltene" refers to a solubility class of crude oil compounds comprising compounds that are filterable after dilution in an aliphatic hydrocarbon medium (e.g., heptane) and which are soluble in an aromatic hydrocarbon medium (e.g., toluene). As used herein, "asphaltenes" include, without limitation, organic salt, organometallic, and graphenic asphaltenes. As used herein, the term "asphaltene inhibitor" includes compounds capable of preventing asphaltene aggregation and/or disaggregating asphaltenes. The person of ordinary skill in the art will appreciate that asphaltene inhibitors may be used in native or processed crude oil matrices (e.g., in an oil production line) to prevent asphaltene deposition (e.g., onto an oil pipeline), or may be used in samples of native or processed crude oil (e.g., in a laboratory setting) to prevent asphaltene deposition (e.g., onto an analytical instrument). A variety of asphaltene inhibitors are available in the art, for example, under the FLOTREAT tradename from Clariant Oil Services, as well as from other organizations including Schlumberger, Halliburton, Nalco, and Akzo Nobel. Asphaltene inhibitors are typically polymeric materials, e.g., p-nonylphenol-formaldehyde polymers.

One aspect of the disclosure is a method for determining a content of disaggregated asphaltene in an inhibited crude oil. The method includes measuring the dielectric constant of the crude oil, the crude oil having a first concentration of an asphaltene inhibitor; providing a first dielectric correction factor for the first concentration of the asphaltene inhibitor; and calculating, e.g., by a computing device, a first corrected dielectric constant of the sample having the first concentration, using the first dielectric correction factor. The method further includes determining the content of disaggregated asphaltene in the first crude oil, based on the first corrected dielectric constant.

An example method (identified in this text as "method 200") of determining the content of disaggregated asphaltene is described. As operation 202, the method 200 may include measuring the dielectric constant of a crude oil, the crude oil having a first concentration of an asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the crude oil comprises water. In certain embodiments of the methods as otherwise described herein, the first concentration is up to about 500 ppm. For example, in certain embodiments of the methods as otherwise described herein, the first concentration is 0 ppm. In another example, in certain embodiments of the methods as otherwise described herein, the first concentration is within the range of about 50 ppm to about 500 ppm. For example, in certain embodiments of the methods as otherwise described herein, the first concentration is within the range of about 50 ppm to about 475 ppm, or about 50 ppm to about 450 ppm, or about 50 ppm to about 425 ppm, or about 50 ppm to about 400 ppm, or about 50 ppm to about 375 ppm, or about 50 ppm to about 350 ppm, or about 50 ppm to about 325 ppm, or about 50 ppm to about 300 ppm, or about 50 ppm to about 275 ppm, or about 50 ppm to about 250 ppm, or about 50 ppm to about 225 ppm, or about 50 ppm to about 200 ppm, or about 50 ppm to about 175 ppm, or about 50 ppm to about 150 ppm, or about 75 ppm to about 500 ppm, or about 100 ppm to about 500 ppm, or about 125 ppm to about 500 ppm, or about 150 ppm to about 500 ppm, or about 175 ppm to about 500 ppm, or about 200 ppm to about 500 ppm, or about 225 ppm to about 500 ppm, or about 250 ppm to about 500 ppm, or about 275 ppm to about 500 ppm, or about 300 ppm to about 500 ppm, or about 325 ppm to about 500 ppm, or about 350 ppm to about 500 ppm, or about 375 ppm to about 500 ppm, or about 400 ppm to about 500 ppm, or about 75 ppm to about 475 ppm, or about 100 ppm to about 450 ppm, or about 125 ppm to about 425 ppm, or about 150 ppm to about 400 ppm, or about 175 ppm to about 375 ppm, or about 200 ppm to about 350 ppm. But the person of ordinary skill in the art will appreciate that the first concentration of asphaltene can be outside these ranges in some embodiments as otherwise described herein.

As operation 204, the method 200 may include providing a first dielectric correction factor for the first concentration of the asphaltene inhibitor. In certain embodiments of the methods as otherwise described herein, the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas.

As operation 206, the method 200 may include calculating, e.g., by a computing device, a first corrected dielectric constant of the first sample having the first concentration, using the first dielectric correction factor. In certain embodiments of the methods as otherwise described herein, calculating the first corrected dielectric constant comprises subtracting the dielectric correction factor from the dielectric constant of the first sample having the first concentration. In certain embodiments, the first corrected dielectric constant may be baseline-corrected (i.e., to provide a corrected "net increase" in dielectric constant).

As operation 208, the method 200 may include determining the content of disaggregated asphaltene in the first crude oil sample, based on the first corrected dielectric constant. For example, in certain embodiments of the methods as otherwise described herein, determining the content of disaggregated asphaltene comprises comparing the first corrected dielectric constant to a predetermined standard curve.

Another aspect of the disclosure is a method for determining an asphaltene inhibition capacity of an asphaltene inhibitor. As used herein, the term "asphaltene inhibition capacity" refers to the extent to which an asphaltene inhibitor prevents asphaltene aggregation in a crude oil, e.g., relative to one or more comparative asphaltene inhibitors. The method includes measuring the dielectric constant of a first sample of a crude oil, the sample having a first concentration of an asphaltene inhibitor; providing a first dielectric correction factor for the first concentration of the asphaltene inhibitor; and calculating, e.g., by a computing device, a first corrected dielectric constant of the first sample having the first concentration, using the first dielectric correction factor. The method further includes measuring the dielectric constant of a second sample of the crude oil, the second sample having a second concentration of the asphaltene inhibitor; providing a second dielectric correction factor for the second concentration of the asphaltene inhibitor; and calculating, e.g., by the computing device, a second corrected dielectric constant of the second sample having the second concentration, using the second dielectric correction factor. The method further includes determining the asphaltene inhibition capacity of the asphaltene inhibitor, based on the second corrected dielectric constant and the first corrected dielectric constant.

An example method of determining an asphaltene inhibition capacity of an asphaltene inhibitor is provided and identified in this text as "method 300." As operation 302, the method 300 may include measuring the dielectric constant of a first crude oil sample, the first sample having a first concentration of an asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the first crude oil sample comprises water. In certain embodiments of the methods as otherwise described herein, the first concentration is up to about 500 ppm. For example, in certain embodiments of the methods as otherwise described herein, the first concentration is 0 ppm. In another example, in certain embodiments of the methods as otherwise described herein, the first concentration is within the range of about 50 ppm to about 500 ppm. In certain such embodiments, the first concentration is within the range of about 50 ppm to about 475 ppm, or about 50 ppm to about 450 ppm, or about 50 ppm to about 425 ppm, or about 50 ppm to about 400 ppm, or about 50 ppm to about 375 ppm, or about 50 ppm to about 350 ppm, or about 50 ppm to about 325 ppm, or about 50 ppm to about 300 ppm, or about 50 ppm to about 275 ppm, or about 50 ppm to about 250 ppm, or about 50 ppm to about 225 ppm, or about 50 ppm to about 200 ppm, or about 50 ppm to about 175 ppm, or about 50 ppm to about 150 ppm, or about 75 ppm to about 500 ppm, or about 100 ppm to about 500 ppm, or about 125 ppm to about 500 ppm, or about 150 ppm to about 500 ppm, or about 175 ppm to about 500 ppm, or about 200 ppm to about 500 ppm, or about 225 ppm to about 500 ppm, or about 250 ppm to about 500 ppm, or about 275 ppm to about 500 ppm, or about 300 ppm to about 500 ppm, or about 325 ppm to about 500 ppm, or about 350 ppm to about 500 ppm, or about 375 ppm to about 500 ppm, or about 400 ppm to about 500 ppm, or about 75 ppm to about 475 ppm, or about 100 ppm to about 450 ppm, or about 125 ppm to about 425 ppm, or about 150 ppm to about 400 ppm, or about 175 ppm to about 375 ppm, or about 200 ppm to about 350 ppm. But the person of ordinary skill in the art will appreciate that the first concentration of asphaltene inhibitor can be outside these ranges in some embodiments as otherwise described herein.

As operation 304, the method 300 may include providing a first dielectric correction factor for the first concentration of the asphaltene inhibitor. In certain embodiments of the methods as otherwise described herein, the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene.

But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas.

As operation 306, the method 300 may include calculating, e.g., by a computing device, a first corrected dielectric constant of the first sample having the first concentration, using the first dielectric correction factor. In certain embodiments of the methods as otherwise described herein, calculating the first corrected dielectric constant comprises subtracting the dielectric correction factor from the dielectric constant of the first sample having the first concentration. In certain embodiments, the first corrected dielectric constant may be baseline-corrected (i.e., to provide a corrected "net increase" in dielectric constant).

As operation 308, the method 300 may include measuring the dielectric constant of a second sample of the crude oil, the second sample having a second concentration of the asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the second crude oil sample comprises water. In certain embodiments of the methods as otherwise described herein, the second concentration is within the range of about 500 ppm to about 2,000 ppm. For example, in certain embodiments of the methods as otherwise described herein, the second concentration is within the range of about 500 ppm to about 1,900 ppm, or about 500 ppm to about 1,800 ppm, or about 500 ppm to about 1,700 ppm, or about 500 ppm to about 1,600 ppm, or about 500 ppm to about 1,500 ppm, or about 500 ppm to about 1,400 ppm, or about 500 ppm to about 1,300 ppm, or about 500 ppm to about 1,200 ppm, or about 500 ppm to about 1,100 ppm, or about 500 ppm to about 1,000 ppm, or about 600 ppm to about 2,000 ppm, or about 700 ppm to about 2,000 ppm, or about 800 ppm to about 2,000 ppm, or about 900 ppm to about 2,000 ppm, or about 1,000 ppm to about 2,000 ppm, or about 1,100 ppm to about 2,000 ppm, or about 1,200 ppm to about 2,000 ppm, or about 1,300 ppm to about 2,000 ppm, or about 1,400 ppm to about 2,000 ppm, or about 1,500 ppm to about 2,000 ppm, or about 600 ppm to about 1,900 ppm, or about 700 ppm to about 1,800 ppm, or about 800 ppm to about 1,700, or about 900 ppm to about 1,600 ppm, or about 1,000 ppm to about 1,500 ppm. But the person of ordinary skill in the art will appreciate that the second concentration of asphaltene inhibitor can be outside these ranges in some embodiments as otherwise described herein.

As operation 310, the method 300 may include providing a second dielectric correction factor for the second concentration of the asphaltene inhibitor. In certain embodiments of the methods as otherwise described herein, the second dielectric correction factor is a weighted average of the dielectric constant of an aliphatic hydrocarbon sample having the second concentration of the asphaltene inhibitor dissolved in an aliphatic hydrocarbon solvent and the dielectric constant of an aromatic hydrocarbon sample having the second concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas. In certain desirable embodiments, the second dielectric correction factor is determined in the using the same solvents and methodology as the first dielectric correction factor.

As operation 312, the method 300 may include calculating, e.g., by a computing device, a second corrected dielectric constant of the second sample having the second concentration, using the second dielectric correction factor. In certain embodiments of the methods as otherwise described herein, calculating the second corrected dielectric constant comprises subtracting the dielectric correction factor from the dielectric constant of the second sample having the second concentration. In certain embodiments, the second corrected dielectric constant may be baseline-corrected (i.e., to provide a corrected "net increase" in dielectric constant).

In certain embodiments of the method 300, operations 302-306 and operations 308-312 may be performed in sequence. For example, in certain embodiments of the methods as otherwise described herein, measuring the dielectric constant of the second crude oil sample having the second concentration of the asphaltene inhibitor is performed after calculating the first corrected dielectric constant of the first crude oil sample having the first concentration of the asphaltene inhibitor. In certain such embodiments, the method may further include adding an amount of the asphaltene inhibitor to the first crude oil sample having the first concentration to provide the second crude oil sample having the second concentration. In other embodiments of the method 300, operations 302-306 and operations 308-312 may be performed in parallel.

As operation 320, the method 300 may include determining the asphaltene inhibition capacity of the asphaltene inhibitor, based on the second corrected dielectric constant and the first corrected dielectric constant. For example, in certain embodiments of the methods as otherwise described herein, determining the asphaltene inhibition capacity comprises comparing the magnitude of the difference between the second corrected dielectric constant and the first corrected dielectric constant to a predetermined standard curve.

In certain embodiments, the method 300 may include, as operation 314, measuring the dielectric constant of a third sample of the crude oil, the third sample having a third concentration of the asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the third crude oil sample comprises water. In certain embodiments of the methods as otherwise described herein, the third concentration is at least about 2,000 ppm. For example, in certain embodiments of the methods as otherwise described herein, the third concentration is at least about 2,100 ppm, at least about 2,200 ppm, at least about 2,300 ppm, at least about 2,400 ppm, at least about 2,500 ppm, at least about 2,750 ppm, at least about 3,000 ppm, at least about 3,250 ppm, at least about 3,500 ppm, at least about 3,750 ppm, at least about 4,000 ppm, at least about 4,250 ppm, at least about 4,500 ppm, at least about 4,750 ppm, or at least about 5,000 ppm, or the third concentration is within the range of about 2,000 ppm to about 3,000 ppm, or about 2,500 ppm to about 3,500 ppm, or about 3,000 ppm to about 4,000 ppm, or about 3,500 ppm to about 4,500 ppm, or about 4,000 ppm to about 5,000 ppm. But the person of ordinary skill in the art will appreciate that the second concentration of asphaltene inhibitor can be outside these ranges in some embodiments as otherwise described herein.

In certain such embodiments, the method 300 may include, as operation 316, providing a third dielectric correction factor for the third concentration of the asphaltene inhibitor. In certain embodiments of the methods as otherwise described herein, the third dielectric correction factor is a weighted average of the dielectric constant of an aliphatic hydrocarbon sample having the third concentration of the asphaltene inhibitor dissolved in an aliphatic hydrocarbon solvent and the dielectric constant of an aromatic hydrocarbon sample having the third concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas. In certain desirable embodiments, the third dielectric correction factor is determined in the using the same solvents and methodology as the first dielectric correction factor and/or the second dielectric correction factor.

In certain such embodiments, the method 300 may include, as operation 318, calculating, e.g., by a computing device, a third corrected dielectric constant of the third sample having the third concentration, using the third dielectric correction factor. In certain embodiments of the methods as otherwise described herein, calculating the third corrected dielectric constant comprises subtracting the dielectric correction factor from the dielectric constant of the third sample having the third concentration. In certain embodiments, the third corrected dielectric constant may be baseline-corrected (i.e., to provide a corrected "net increase" in dielectric constant).

In certain such embodiments of the method 300, operations 302-312 and operations 314-318 may be performed in sequence. For example, in certain embodiments of the methods as otherwise described herein, measuring the dielectric constant of the third crude oil sample having the third concentration of the asphaltene inhibitor is performed after calculating the second corrected dielectric constant of the second sample having the second concentration of the asphaltene inhibitor. In certain such embodiments, the method may further include adding an amount of the asphaltene inhibitor to the second crude oil sample having the second concentration to provide the third crude oil sample having the third concentration. In other embodiments of the method 300, operations 302-312 and operations 314-318 may be performed in parallel.

In certain embodiments of the method 300, determining the asphaltene inhibition capacity of the asphaltene inhibitor (operation 320) is further based on the third corrected dielectric constant. For example, in certain embodiments of the methods as otherwise described herein, determining the asphaltene inhibition capacity comprises fitting the first corrected dielectric constant, the second corrected dielectric constant, and the third corrected dielectric constant to a linear function. In another example, in certain embodiments of the methods as otherwise described herein, determining the asphaltene inhibition capacity comprises fitting the first corrected dielectric constant, the second corrected dielectric constant, and the third corrected dielectric constant (i.e., corrected dielectric constant as a function of concentration of asphaltene inhibitor) to a polynomial function, such as a parabolic function. But the person of ordinary skill in the art will appreciate that other mathematical functions can be used in the fitting of the corrected dielectric constants. Moreover, the person of ordinary skill in the art will appreciate that additional corrected dielectric constants can be determined and used to fit a function of corrected dielectric constant vs. concentration of asphaltene inhibitor. For example, four, five, six, seven, eight, nine, or 10 concentrations can be used. Multiple replicates can be measured at each concentration of asphaltene inhibitor; conventional numerical methods can be used in fitting them to a function as described above.

Another aspect of the disclosure is a method for selecting one or more target asphaltene inhibitors for use in the inhibition of asphaltenes in a crude oil matrix. In certain embodiments of the methods as otherwise described herein, the crude oil matrix may be, for example, the native crude oil matrix of an oil production line. The method includes providing a plurality of asphaltene inhibitors (e.g., 2, 3, 4, 5, or more asphaltene inhibitors), and for each asphaltene inhibitor of the plurality, determining an asphaltene inhibition capacity for a crude oil (e.g., of a crude oil matrix) according to methods of the disclosure as otherwise described herein (e.g., according to method 300). The method further includes selecting, from the plurality, inhibitors having an asphaltene inhibition capacity above a predetermined cutoff, to provide one or more target asphaltene inhibitors for the crude oil.

Another aspect of the disclosure is a method for determining an effective asphaltene inhibitor concentration for a crude oil matrix. As used herein, the term "effective asphaltene inhibitor concentration" refers to a concentration of asphaltene inhibitor at which a crude oil matrix is suitable for use in, e.g., an oil production line, laboratory setting, etc. In certain embodiments, the method is for determining a minimum effective asphaltene inhibitor concentration for the crude oil matrix. As used herein, the term "minimum effective asphaltene inhibitor concentration" refers to the lowest concentration of asphaltene inhibitor at which a crude oil matrix is suitable for use in, e.g., an oil production line, laboratory setting, etc. The method includes measuring the dielectric constant of a first sample of the crude oil, the first sample having a first concentration of an asphaltene inhibitor; providing a first dielectric correction factor for the first concentration of the asphaltene inhibitor; and calculating, e.g., by a computing device, a first corrected dielectric constant of the first sample having the first concentration, using the first dielectric correction factor. The method further includes measuring the dielectric constant of a second sample of the crude oil, the second sample having a second concentration of the asphaltene inhibitor; providing a second dielectric correction factor for the second concentration of the asphaltene inhibitor; and calculating, e.g., by the computing device, a second corrected dielectric constant of the sample having the second concentration, using the second dielectric correction factor. The method further includes calculating, e.g., by the computing device, based on the first corrected dielectric constant and the second corrected dielectric constant, an effective concentration (e.g., a minimum concentration) of the asphaltene inhibitor sufficient to provide a predetermined minimum corrected dielectric constant, or a predetermined minimum net increase in corrected dielectric constant. An example method of determining an effective (e.g., a minimum effective) asphaltene inhibitor concentration for a crude oil matrix is described below and identified as "method 400."

As operation 402, the method 400 may include measuring the dielectric constant of a first sample of the crude oil, the first sample having a first concentration of an asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the first crude oil sample comprises water. In certain embodiments of the methods as otherwise described herein, the first concentration is up to about 500 ppm. For example, in certain embodiments of the methods as otherwise described herein, the first concentration is 0 ppm. In another example, in certain embodiments of the methods as otherwise described herein, the first concentration is within the range of about 50 ppm to about 500 ppm. In certain such embodiments, the first concentration is within the range of about 50 ppm to about 475 ppm, or about 50 ppm to about 450 ppm, or about 50 ppm to about 425 ppm, or about 50 ppm to about 400 ppm, or about 50 ppm to about 375 ppm, or about 50 ppm to about 350 ppm, or about 50 ppm to about 325 ppm, or about 50 ppm to about 300 ppm, or about 50 ppm to about 275 ppm, or about 50 ppm to about 250 ppm, or about 50 ppm to about 225 ppm, or about 50 ppm to about 200 ppm, or about 50 ppm to about 175 ppm, or about 50 ppm to about 150 ppm, or about 75 ppm to about 500 ppm, or about 100 ppm to about 500 ppm, or about 125 ppm to about 500 ppm, or about 150 ppm to about 500 ppm, or about 175 ppm to about 500 ppm, or about 200 ppm to about 500 ppm, or about 225 ppm to about 500 ppm, or about 250 ppm to about 500 ppm, or about 275 ppm to about 500 ppm, or about 300 ppm to about 500 ppm, or about 325 ppm to about 500 ppm, or about 350 ppm to about 500 ppm, or about 375 ppm to about 500 ppm, or about 400 ppm to about 500 ppm, or about 75 ppm to about 475 ppm, or about 100 ppm to about 450 ppm, or about 125 ppm to about 425 ppm, or about 150 ppm to about 400 ppm, or about 175 ppm to about 375 ppm, or about 200 ppm to about 350 ppm. But the person of ordinary skill in the art will appreciate that the first concentration of asphaltene inhibitor can be outside these ranges in some embodiments as otherwise described herein.

As operation 404, the method 400 may include providing a first dielectric correction factor for the first concentration of the asphaltene inhibitor. In certain embodiments of the methods as otherwise described herein, the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas.

As operation 406, the method 400 may include calculating, e.g., by a computing device, a first corrected dielectric constant of the sample having the first concentration, using the first dielectric correction factor. In certain embodiments of the methods as otherwise described herein, calculating the first corrected dielectric constant comprises subtracting the dielectric correction factor from the dielectric constant of the sample having the first concentration. In certain embodiments, the first corrected dielectric constant may be baseline-corrected (i.e., to provide a corrected "net increase" in dielectric constant).

As operation 408, the method 400 may include measuring the dielectric constant of a second sample of the crude oil, the second sample having a second concentration of the asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the second crude oil sample comprises water. In certain embodiments of the methods as otherwise described herein, the second concentration is within the range of about 500 ppm to about 2,000 ppm. For example, in certain embodiments of the methods as otherwise described herein, the second concentration is within the range of about 500 ppm to about 1,900 ppm, or about 500 ppm to about 1,800 ppm, or about 500 ppm to about 1,700 ppm, or about 500 ppm to about 1,600 ppm, or about 500 ppm to about 1,500 ppm, or about 500 ppm to about 1,400 ppm, or about 500 ppm to about 1,300 ppm, or about 500 ppm to about 1,200 ppm, or about 500 ppm to about 1,100 ppm, or about 500 ppm to about 1,000 ppm, or about 600 ppm to about 2,000 ppm, or about 700 ppm to about 2,000 ppm, or about 800 ppm to about 2,000 ppm, or about 900 ppm to about 2,000 ppm, or about 1,000 ppm to about 2,000 ppm, or about 1,100 ppm to about 2,000 ppm, or about 1,200 ppm to about 2,000 ppm, or about 1,300 ppm to about 2,000 ppm, or about 1,400 ppm to about 2,000 ppm, or about 1,500 ppm to about 2,000 ppm, or about 600 ppm to about 1,900 ppm, or about 700 ppm to about 1,800 ppm, or about 800 ppm to about 1,700, or about 900 ppm to about 1,600 ppm, or about 1,000 ppm to about 1,500 ppm. But the person of ordinary skill in the art will appreciate that the second concentration of asphaltene inhibitor can be outside these ranges in some embodiments as otherwise described herein.

As operation 410, the method 400 may include providing a second dielectric correction factor for the second concentration of the asphaltene inhibitor. In certain embodiments of the methods as otherwise described herein, the second dielectric correction factor is a weighted average of the dielectric constant of an aliphatic hydrocarbon sample having the second concentration of the asphaltene inhibitor dissolved in an aliphatic hydrocarbon solvent and the dielectric constant of an aromatic hydrocarbon sample having the second concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas. In certain desirable embodiments, the second dielectric correction factor is determined in the using the same solvents and methodology as the first dielectric correction factor.

As operation 412, the method 400 may include calculating, e.g., by a computing device, a second corrected dielectric constant of the sample having the second concentration, using the second dielectric correction factor. In certain embodiments of the methods as otherwise described herein, calculating the second corrected dielectric constant comprises subtracting the dielectric correction factor from the dielectric constant of the sample having the second concentration. In certain embodiments, the second corrected dielectric constant may be baseline-corrected (i.e., to provide a corrected "net increase" in dielectric constant).

In certain embodiments of the method 400, operations 402-406 and operations 408-412 may be performed in sequence. For example, in certain embodiments of the methods as otherwise described herein, measuring the dielectric constant of the second crude oil sample having the second concentration of the asphaltene inhibitor is performed after calculating the first corrected dielectric constant of the first crude oil sample having the first concentration of an asphaltene inhibitor. In certain such embodiments, the method may further include adding an amount of the asphaltene inhibitor to the first crude oil sample having the first concentration to provide the second crude oil sample having the second concentration. In other embodiments of the method 400, operations 402-406 and operations 408-412 may be performed in parallel.

As operation 420, the method 400 may include calculating, e.g., by the computing device, based on the first corrected dielectric constant and the second corrected dielectric constant, an effective (e.g., minimum) concentration of the asphaltene inhibitor. In certain embodiments of the methods as otherwise described herein, the effective concentration of the asphaltene inhibitor is a concentration sufficient to provide at least a predetermined minimum corrected dielectric constant. The minimum concentration is the minimum concentration sufficient to provide the predetermined minimum corrected dielectric constant. For example, in certain embodiments of the methods as otherwise described herein, the minimum corrected dielectric constant is at least about 15, at least about 16, at least about 17, at least about 18, or at least about 19. In certain embodiments of the methods as otherwise described herein, the minimum concentration of the asphaltene inhibitor is a concentration sufficient to provide a predetermined minimum net increase in corrected dielectric constant. For example, in certain embodiments of the methods as otherwise described herein, the minimum net increase in corrected dielectric constant is at least about 10, at least about 11, at least about 12, at least about 13, or at least about 14.

In certain embodiments, the method 400 may include, as operation 414, measuring the dielectric constant of a third sample of the crude oil, the third sample having a third concentration of the asphaltene inhibitor. In certain embodiments of the methods as otherwise described herein, measuring the dielectric constant comprises measuring with a capacitor, e.g., a cylindrical capacitor. In certain embodiments of the methods as otherwise described herein, the third crude oil sample comprises water. In certain embodiments of the methods as otherwise described herein, the third concentration is at least about 2,000 ppm. For example, in certain embodiments of the methods as otherwise described herein, the third concentration is at least about 2,100 ppm, at least about 2,200 ppm, at least about 2,300 ppm, at least about 2,400 ppm, at least about 2,500 ppm, at least about 2,750 ppm, at least about 3,000 ppm, at least about 3,250 ppm, at least about 3,500 ppm, at least about 3,750 ppm, at least about 4,000 ppm, at least about 4,250 ppm, at least about 4,500 ppm, at least about 4,750 ppm, or at least about 5,000 ppm, or the third concentration is within the range of about 2,000 ppm to about 3,000 ppm, or about 2,500 ppm to about 3,500 ppm, or about 3,000 ppm to about 4,000 ppm, or about 3,500 ppm to about 4,500 ppm, or about 4,000 ppm to about 5,000 ppm. But the person of ordinary skill in the art will appreciate that the third concentration of asphaltene inhibitor can be outside these ranges in some embodiments as otherwise described herein.

In certain such embodiments, the method 400 may include, as operation 416, providing a third dielectric correction factor for the third concentration of the asphaltene inhibitor. In certain embodiments of the methods as otherwise described herein, the third dielectric correction factor is a weighted average of the dielectric constant of an aliphatic hydrocarbon sample having the third concentration of the asphaltene inhibitor dissolved in an aliphatic hydrocarbon solvent and the dielectric constant of an aromatic hydrocarbon sample having the third concentration of the asphaltene inhibitor dissolved in an aromatic hydrocarbon solvent. In certain such embodiments, the average is evenly weighted. In certain such embodiments, the aliphatic hydrocarbon solvent of the aliphatic hydrocarbon sample is heptane (e.g., n-heptane) and/or the aromatic hydrocarbon solvent of the hydrocarbon sample is toluene. But the person of ordinary skill in the art will appreciate that other aliphatic hydrocarbon solvents can be used, e.g., n-octane, isooctane, gasoline, kerosene, VM&P naphtha, mineral spirits. Similarly, the person of ordinary skill in the art will appreciate that other aromatic hydrocarbon solvents can be used, e.g., xylenes, ethylbenzene, high-flash aromatic naphthas. In certain desirable embodiments, the third dielectric correction factor is determined in the using the same solvents and methodology as the first dielectric correction factor and/or the second dielectric correction factor.

In certain such embodiments, the method 400 may include, as operation 418, calculating, e.g., by a computing device, a third corrected dielectric constant of the sample having the third concentration, using the third dielectric correction factor. In certain embodiments of the methods as otherwise described herein, calculating the third corrected dielectric constant comprises subtracting the dielectric correction factor from the dielectric constant of the sample having the third concentration. In certain embodiments, the third corrected dielectric constant may be baseline-corrected (i.e., to provide a corrected "net increase" in dielectric constant).

In certain such embodiments of the method 400, operations 402-412 and operations 414-418 may be performed in sequence. For example, in certain embodiments of the methods as otherwise described herein, measuring the dielectric constant of the third crude oil sample having the third concentration of the asphaltene inhibitor is performed after calculating the second corrected dielectric constant of the sample having the second concentration of an asphaltene inhibitor. In certain such embodiments, the method may further include adding an amount of the asphaltene inhibitor to the second crude oil sample having the second concentration to provide the third crude oil sample having the third concentration. In other embodiments of the method 400, operations 402-412 and operations 414-418 may be performed in parallel.

In certain such embodiments of the method 400, determining the asphaltene inhibition capacity of the asphaltene inhibitor (operation 420) is further based on the third corrected dielectric constant.

Another aspect of the disclosure is a method for inhibiting a crude oil e.g., in a crude oil matrix. In certain embodiments of the methods as otherwise described herein, the method for inhibiting a crude oil (e.g., of a native crude oil matrix of an oil production line) comprises of determining an effective asphaltene inhibitor concentration, for example, a minimum effective asphaltene inhibitor concentration (e.g., according to a method as otherwise described herein), and adding an amount of the asphaltene inhibitor to the crude oil matrix sufficient to provide an inhibitor concentration of at least that effective asphaltene inhibitor concentration. For example, in certain embodiments of the methods as otherwise described herein, the method for inhibiting a crude oil matrix includes determining an effective (e.g., a minimum effective) asphaltene inhibitor concentration according to a method as described herein, for example, method 400.

In certain embodiments of the methods as otherwise described herein, the method for inhibiting a crude oil (e.g., of a native crude oil matrix of an oil production line) comprises selecting one or more target asphaltene inhibitors (e.g., according to a method as otherwise described herein), and adding an amount of a target asphaltene inhibitor to the crude oil. In certain embodiments of the methods as otherwise described herein, selecting one or more inhibitors includes providing a plurality of asphaltene inhibitors (e.g., 2, 3, 4, 5, or more asphaltene inhibitors), and for each inhibitor of the plurality, determining an asphaltene inhibition capacity for a crude oil according to methods of the disclosure as otherwise described herein (e.g., according to method 300). In certain such embodiments, selecting one or more inhibitors includes selecting, from the plurality, inhibitors having an asphaltene inhibition capacity above a predetermined cutoff, to provide one or more target asphaltene inhibitors for the crude oil. In certain embodiments of the methods as otherwise described herein, the method includes, before adding an amount of the target asphaltene inhibitor to the crude oil, determining an effective (e.g., a minimum effective asphaltene inhibitor concentration (e.g., for a crude oil sample of the crude oil matrix, according to a method as otherwise described herein, e.g., according to method 400). In certain such embodiments, the amount of the target asphaltene added to the crude oil is sufficient to provide an inhibitor concentration of at least the minimum effective asphaltene inhibitor concentration.

Another aspect of the disclosure is a non-transitory computer-readable medium having stored thereon program instructions that when executed by a processor of a computing device cause the computing device to perform a set of functions. The set of functions can be any set of functions as described with respect to the methods described above, in which the measurement of dielectric constant is replaced by the receiving of the measured dielectric constant. For example, in certain embodiments, the set of functions includes receiving a first dielectric constant of a first sample of a crude oil, the first sample having a first concentration of an asphaltene inhibitor; and calculating a first corrected dielectric constant of the sample having the first concentration, using a first dielectric correction factor. The set of functions further comprises receiving a second dielectric constant of a second sample of the crude oil, the second sample having a second concentration of the asphaltene inhibitor and calculating a second corrected dielectric constant of the sample having the second concentration, using a second dielectric correction factor. An example set of functions that may be stored on a non-transitory computer-readable medium (e.g., the data storage of the computing device) is described below and identified as "set 500."

As operation 502, the set 500 may include receiving (e.g., at the input/output function of the computing device) a first dielectric constant of a first crude oil sample, the first crude oil sample having a first concentration of an asphaltene inhibitor. In certain embodiments of the medium as otherwise described herein, receiving the dielectric constant is from a dielectric constant measuring device, e.g., a capacitor such as a cylindrical capacitor. In other embodiments of the medium as otherwise described herein, receiving the dielectric constant is from a user input device, e.g., a keyboard or mouse. The first crude oil sample and the first concentration of asphaltene inhibitor can be as otherwise described herein.

As operation 510, the set 500 may include calculating a first corrected dielectric constant of the sample having the first concentration, using a first dielectric correction factor. In certain embodiments of the medium as otherwise described herein, calculating the first corrected dielectric constant comprises subtracting the dielectric correction factor from the dielectric constant of the sample having the first concentration. In certain embodiments of the medium as otherwise described herein, the first dielectric correction factor is a predetermined value (e.g., stored on the data storage of the computing device). In certain embodiments, the first corrected dielectric constant may be baseline-corrected (i.e., to provide a corrected "net increase" in dielectric constant).

In certain embodiments, the set 500 may include, as operation 504, receiving a dielectric constant of an aliphatic hydrocarbon sample having the first concentration of the asphaltene inhibitor. In certain such embodiments, the set 500 may include, as operation 506, receiving a dielectric constant of an aromatic hydrocarbon sample having the first concentration of the asphaltene inhibitor. In certain embodiments of the medium as otherwise described herein, receiving the dielectric constant is from a dielectric constant measuring device, e.g., a cylindrical capacitor. In other embodiments of the medium as otherwise described herein, receiving the dielectric constant is from a user input device, e.g., a keyboard or mouse. In certain embodiments, the set 500 may include, as operation 508, calculating the first dielectric correction factor, using the dielectric constant of the aliphatic hydrocarbon sample having the first concentration and the dielectric constant of the aromatic hydrocarbon sample having the first concentration. The aliphatic hydrocarbon sample, the aliphatic aromatic sample, and the calculation of the first dielectric factor can be as otherwise described herein.

As operation 512, the set 500 may include receiving (e.g., at the input/output function of the computing device) a second dielectric constant of a second crude oil sample, the sample having a second concentration of an asphaltene inhibitor. The receiving of the second dielectric constant can be as described above with respect to receiving the first dielectric constant, and the second crude oil sample and the second concentration of asphaltene inhibitor can be as otherwise described herein.

As operation 520, the set 500 may include calculating a second corrected dielectric constant of the sample having the second concentration, using a second dielectric correction factor. In certain embodiments of the medium as otherwise described herein, calculating the second corrected dielectric constant comprises subtracting the dielectric correction factor from the dielectric constant of the sample having the second concentration. In certain embodiments of the medium as otherwise described herein, the second dielectric correction factor is a predetermined value (e.g., stored on the data storage of computing device). In certain embodiments, the second corrected dielectric constant may be baseline-corrected (i.e., to provide a corrected "net increase" in dielectric constant).

In certain embodiments, the set 500 may include, as operation 514, receiving a dielectric constant of an aliphatic hydrocarbon sample having the second concentration of the asphaltene inhibitor. In certain such embodiments, the set 500 may include, as operation 516, receiving a dielectric constant of an aromatic hydrocarbon sample having the second concentration of the asphaltene inhibitor. In certain embodiments of the medium as otherwise described herein, receiving the dielectric constant is from a dielectric constant measuring device, e.g., a cylindrical capacitor. In other embodiments of the medium as otherwise described herein, receiving the dielectric constant is from a user input device, e.g., a keyboard or mouse. In certain embodiments, the set 500 may include, as operation 518, calculating the second dielectric correction factor, using the dielectric constant of the aliphatic sample having the second concentration and the dielectric constant of the aromatic hydrocarbon sample having the second concentration. The aliphatic hydrocarbon sample, the aliphatic aromatic sample, and the calculation of the second dielectric factor can be as otherwise described herein.

In certain embodiments of the set 500, operations 502-510 and operations 512-520 may be performed in sequence. For example, in certain embodiments of the medium as otherwise described herein, receiving the second dielectric constant is performed after calculating the first corrected dielectric constant. In other embodiments of the set 500, operations 502-510 and operations 512-520 may be performed in parallel.

As operation 532, the set 500 may include calculating a first magnitude of the difference between the second corrected dielectric constant and the first corrected dielectric constant.

As operation 534, the set 500 may include determining an asphaltene inhibition capacity, based on the first magnitude. In certain embodiments of the medium as otherwise described herein, determining an asphaltene inhibition capacity comprises comparing the magnitude to a predetermined standard (e.g., stored on the data storage of the computing device).

In certain embodiments, the set 500 may include, as operation 522, receiving (e.g., at the input/output function of the computing device) a third dielectric constant of a third sample of the crude oil, the third sample having a third concentration of an asphaltene inhibitor. The receiving of the third dielectric constant can be as described above with respect to receiving the first dielectric constant, and the third crude oil sample and the third concentration of asphaltene inhibitor can be as otherwise described herein.

As operation 530, the set 500 may include calculating a third corrected dielectric constant of the sample having the third concentration, using a third dielectric correction factor. In certain embodiments of the medium as otherwise described herein, calculating the third corrected dielectric constant comprises subtracting the dielectric correction factor from the dielectric constant of the sample having the third concentration. In certain embodiments of the medium as otherwise described herein, the third dielectric correction factor is a predetermined value (e.g., stored on the data storage of the computing device). In certain embodiments, the third corrected dielectric constant may be baseline-corrected (i.e., to provide a corrected "net increase" in dielectric constant).

In certain embodiments, the set 500 may include, as operation 524, receiving a dielectric constant of an aliphatic hydrocarbon sample having the third concentration of the asphaltene inhibitor. In certain such embodiments, the set 500 may include, as operation 526, receiving a dielectric constant of an aromatic hydrocarbon sample having the third concentration of the asphaltene inhibitor. In certain embodiments of the medium as otherwise described herein, receiving the dielectric constant is from a dielectric constant measuring device, e.g., a cylindrical capacitor. In other embodiments of the medium as otherwise described herein, receiving the dielectric constant is from a user input device, e.g., a keyboard or mouse. The aliphatic hydrocarbon sample, the aliphatic aromatic sample, and the calculation of the third dielectric factor can be as otherwise described herein.

In certain embodiments of the set 500, operations 502-520 and operations 522-530 may be performed in sequence. For example, in certain embodiments of the medium as otherwise described herein, receiving the third dielectric constant is performed after calculating the second corrected dielectric constant. In other embodiments of the set 500, operations 502-520 and operations 522-530 may be performed in parallel.

In certain embodiments, the set 500 may include, as operation 536, calculating a trend using the first corrected dielectric constant, the second corrected dielectric constant, and the third corrected dielectric constant. For example, in certain embodiments of the medium as otherwise described herein, calculating the trend comprises fitting the corrected dielectric constants (i.e., corrected dielectric constant as a function of concentration of asphaltene inhibitor) to a linear function. In another example, in certain embodiments of the medium as otherwise described herein, calculating the trend comprises fitting the dielectric constants to a polynomial function (e.g., a parabolic function). But the person of ordinary skill in the art will appreciate that other mathematical functions can be used in the fitting of the corrected dielectric constants. Moreover, the person of ordinary skill in the art will appreciate that additional corrected dielectric constants can be determined and used to fit a function of corrected dielectric constant vs. concentration of asphaltene inhibitor. For example, four, five, six, seven, eight, nine, or 10 concentrations can be used. Multiple replicates can be measured at each concentration of asphaltene inhibitor; conventional numerical methods can be used in fitting them to a function as described above. In certain such embodiments, the set 500 may include, as operation 538, determining an asphaltene inhibition capacity of the asphaltene inhibitor, based on the trend.

Dielectric constants of crude oil samples can be measured as described in U.S. Patent Application Publication no. 2018/0024084, which is hereby incorporated herein by reference in its entirety. A cylindrical capacitor as described therein can be configured in a single device together with a processor as described herein. For example, one embodiment of the disclosure is a cylindrical capacitor as described in U.S. Patent Application Publication no. 2018/0024084, configured to provide dielectric constant measurements to a processor programmed (e.g., with a non-transitory computer medium as described herein) to perform the calculations described herein.

EXAMPLES

The Examples that follow are illustrative of specific embodiments of the disclosure, and various uses thereof. They are set forth for explanatory purposes only and are not to be taken as limiting the scope of the disclosure.

Example 1. Determination of Inhibitor Properties of Chemical A

A known good asphaltene inhibitor, Chemical A, was added at concentrations ranging from 100 ppm to 5000 ppm, a dosage range that could be used in the field, to four crude oils and two solvents. The dielectric constant of the fluid was measured after each addition.

Three of the crude oils, A, B and D, were nominally dry. The fourth, C, was wet, containing 16% produced brine as a stable emulsion. All four were known to contain asphaltenes that could deposit under production conditions and that would precipitate and sediment when the oil was added to heptane.

The two solvents were toluene, representing the aromatic hydrocarbon components of crude oil, which dissolve asphaltenes, and heptane, representing the aliphatic hydrocarbon constituents of crude oil, which precipitate asphaltenes. The mixture of hydrocarbons in the crude oil samples had properties somewhere between these two solvents.

The results are shown in Table 1, below. As Chemical A was added to the solvents, the dielectric constant of the toluene barely increased, in a reverse parabolic fashion, and that of the heptane increased negligibly. These small increases in the dielectric constant induced by adding Chemical A (in the absence of asphaltenes) are summarized in Table 2, below. Subtracting the average of the dielectric constant increases in heptane and toluene from the increases in the crude oils gave the net increase in the dielectric constant due to the effect of the chemical on the asphaltenes. This is shown in Table 3, below.

TABLE 1

Effect of Chemical A on the Dielectric Constant of Crude Oils and Solvents

| Dosage (ppm) | Dry Oil A | | Dry Oil B | | D | Wet Oil C | | Tol. | Hept. |
|---|---|---|---|---|---|---|---|---|---|
| 0 | 6.11 | 5.92 | 6.23 | 5.59 | 5.01 | 4.90 | 4.63 | 2.45 | 1.91 |
| 100 | 9.95 | 8.56 | 6.89 | 6.03 | 10.37 | 6.37 | | 2.42 | 1.68 |
| 200 | 11.90 | 8.82 | 8.02 | 8.21 | 19.14 | 6.33 | | | |
| 300 | 16.40 | 14.31 | 9.12 | 8.05 | 27.47 | 7.08 | | | |
| 400 | 18.45 | 16.03 | 12.57 | 11.90 | 25.34 | 7.34 | | | |
| 500 | 17.90 | 17.94 | 16.38 | 17.38 | 33.86 | 7.94 | | 2.88 | 1.86 |
| 600 | 20.89 | 21.41 | | | 42.05 | | | | |

TABLE 1-continued

Effect of Chemical A on the Dielectric Constant of Crude Oils and Solvents

| Dosage | Dry Oil | | | Wet Oil | Solvents | |
|---|---|---|---|---|---|---|
| (ppm) | A | B | D | C | Tol. | Hept. |
| 700 | 37.45 | 32.75 | | 66.71 | | |
| 800 | 34.33 | 31.50 | | 52.73 | | |
| 900 | 44.43 | 40.46 | | 63.74 | | |
| 1,000 | 62.72 | 56.60 | 16.33 | 73.75 | 3.34 | 1.96 |
| 1,500 | 88.68 | | 32.37 | | | |
| 1,700 | | | 29.73 | | | |
| 2,000 | | | 40.77 | | | |
| 2,500 | | | 58.93 | | | |
| 5,000 | | | 188.99 | | 4.36 | 2.13 |

TABLE 2

Correction for Effect of Chemical A in Solvent

| ppm | Toluene | Heptane | Average |
|---|---|---|---|
| 100 | 0.11 | 0.01 | 0.06 |
| 200 | 0.21 | 0.01 | 0.11 |
| 300 | 0.31 | 0.02 | 0.16 |
| 400 | 0.41 | 0.03 | 0.22 |
| 500 | 0.50 | 0.03 | 0.27 |
| 600 | 0.60 | 0.04 | 0.32 |
| 700 | 0.69 | 0.04 | 0.37 |
| 800 | 0.77 | 0.05 | 0.41 |
| 900 | 0.86 | 0.06 | 0.46 |
| 1,000 | 0.94 | 0.06 | 0.50 |
| 1,500 | 1.30 | 0.10 | 0.70 |
| 1,700 | 1.43 | 0.11 | 0.77 |
| 2,000 | 1.60 | 0.13 | 0.86 |
| 2,500 | 1.82 | 0.16 | 0.99 |
| 5,000 | 1.89 | 0.32 | 1.11 |

TABLE 3

Net Effect of Chemical A on Dielectric Constant of Crude Oils

| Dosage | Dry Oil | | | Wet Oil |
|---|---|---|---|---|
| (ppm) | A | B | D | C |
| 100 | 3.88 | 2.49 | 0.92 | 0.06 | 5.30 | 1.55 |
| 200 | 5.77 | 2.69 | 2.00 | 2.19 | 14.02 | 1.45 |
| 300 | 10.22 | 8.13 | 3.05 | 1.98 | 22.30 | 2.15 |
| 400 | 12.22 | 9.80 | 6.44 | 5.77 | 20.11 | 2.36 |
| 500 | 11.62 | 11.66 | 10.20 | 11.20 | 28.58 | 2.91 |
| 600 | 14.56 | 15.08 | | | 36.72 | |
| 700 | 31.07 | 26.37 | | | 61.33* | |
| 800 | 27.90 | 25.07 | | | 47.31 | |
| 900 | 37.96 | 33.99 | | | 58.27 | |
| 1000 | 56.20 | 50.08 | 9.92 | | 68.24 | |
| 1500 | 81.97 | | 25.76 | | | |
| 1700 | | | 23.05 | | | |
| 2000 | | | 34.00 | | | |
| 2500 | | | 52.03 | | | |
| 5000 | | | 181.97 | | | |
| Avg. Blank | 6.02 | | 5.91 | | 5.01 | 4.77 |

*Value outside error range - not included in numerical analysis below.

Without intending to be bound by theory, the present inventors believe that the increase of the dielectric constant of the crude oil over the increase observed in toluene or heptane is due to a shift from aggregated asphaltenes, the dielectric contributions of which can cancel out (for example, in a symmetric micelle), to disaggregated asphaltenes, which can contribute to the dielectric constant of the sample to a greater extent.

The data of Table 3 show that the net increases in the dielectric constant of the three dry crude oils (A, B, D) rose dramatically, in a generally parabolic fashion, with increased dosage of Chemical A. The wet crude oil (C) increased far less, and in a linear fashion. Advantageously, this in itself is a useful characterization of the crude oil. Differences in the rate of increase are a function of the amount and dispersibility of aggregated asphaltenes in the crude oil samples, and therefore are a function of the difficulty of inhibiting asphaltene deposition in their production. The dielectric response can be summarized by the parameters of the parabolic curves, provided in Table 4, below. Notably, the response of the dielectric constant of the crude oil sample to the chemical was neither related nor correlated to the baseline dielectric constant of the crude.

TABLE 4

Chemical A Net Dielectric Response Parabolic Parameters

| Dielectric Parameters | Oil A | Oil B | Oil D | Oil C |
|---|---|---|---|---|
| Avg Blank (baseline) | 6.015 | 5.910 | 5.010 | 4.765 |
| y Intercept | (0.163) | 1.627 | 1.609 | 0.309 |
| x coefficient | 1.709 | 0.432 | 4.681 | 0.550 |
| $x^2$ coefficient | 0.270 | 0.063 | 0.179 | — |
| Correlation coefficient | 0.979 | 0.998 | 0.993 | 0.949 |

The wet crude did not respond well to Chemical A. It is well known that produced water breakthrough dramatically reduces the effectiveness of asphaltene inhibitors. In an emulsion, the asphaltenes are not aggregated with each other in the oil, but rather are adsorbed onto the water droplet surface, from which they are more difficult to solubilize. Conventional crude oil asphaltene characterization techniques are not capable of measuring this emulsified water effect.

Different chemicals have different effects on a given crude oil's asphaltenes. The effect of several different chemicals on the dielectric constant of crude oil B and of the base solvents, toluene and heptane, is shown in Table 5, below. The net change in the dielectric constant of the crude oil from the addition of the chemical, after subtracting the average effect of the chemical on the solvents and the baseline dielectric constant of the crude oil, is also shown in Table 5.

TABLE 5

Effect on Dielectric Constant of Different Chemicals Added at 500 ppm

| Chem. | Dielectric Constant | | | Change in Dielectric Constant | | | | Net Effect on B |
|---|---|---|---|---|---|---|---|---|
| | Oil B | Tol. | Hept. | Oil B | Tol. | Hept. | Avg. | |
| Blank | 5.91 | 2.45 | 1.91 | — | — | — | — | — |
| A | 16.88 | 2.88 | 1.86 | 10.97 | 0.43 | (0.05) | 0.19 | 10.78 |
| B | 14.33 | 6.00 | 1.68 | 8.42 | 3.55 | (0.23) | 1.66 | 6.76 |
| C | 16.89 | 5.96 | 1.81 | 10.98 | 3.51 | (0.10) | 1.71 | 9.28 |
| D | 12.36 | 4.26 | 1.96 | 6.45 | 1.81 | 0.05 | 0.93 | 5.52 |
| E | 6.71 | 2.55 | 1.48 | 0.80 | 0.10 | (0.43) | (0.17) | 0.97 |
| F | 8.03 | 4.63 | 2.89 | 2.12 | 2.18 | 0.98 | 1.58 | 0.54 |

Example 2. Comparison to Conventional Sedimentation Method

A conventional method for measuring the effects of an asphaltene inhibitor on crude oil samples is to force the precipitation of the asphaltenes by diluting the crude oil in 10-100 times the amount of heptane and measure the extent to and speed with which precipitated asphaltenes aggregate and sink to the bottom of a tube. The extent of the separation ("Separability Number", SN, as the percent difference between successive layers) and the rate of that separation ("Sedimentation Velocity", SV, in μm/s) for a wide variety of crude oils and chemicals are listed in Table 6, below.

TABLE 6

Comparison of Dielectric and Forced Separation Parameters

| ppm | Oil | Dielectric Constant | Net Increase in DC | Sep. No. | Sed. Vel. | Sep. Pot. | Decrease in SP |
|---|---|---|---|---|---|---|---|
| 0 | A | 5.92 | | 11.34 | 312.40 | 17.26 | |
| | | 6.02 | | | | | |
| | | 6.11 | | | | | |
| 100 | A | 8.50 | 2.43 | 9.95 | 189.70 | 12.71 | 4.55 |
| | | 9.26 | 3.18 | | | | |
| | | 9.89 | 3.82 | | | | |
| 200 | A | 8.71 | 2.58 | 3.86 | 65.61 | 4.73 | 12.53 |
| | | 10.36 | 4.23 | | | | |
| | | 11.79 | 5.66 | | | | |
| 300 | A | 14.15 | 7.97 | 0.97 | 36.79 | 1.81 | 15.45 |
| | | 15.36 | 9.18 | | | | |
| | | 16.24 | 10.06 | | | | |
| 400 | A | 15.81 | 9.58 | 0.60 | 3.89 | 0.62 | 16.64 |
| | | 17.24 | 11.01 | | | | |
| | | 18.23 | 12.00 | | | | |
| 500 | A | 17.63 | 11.35 | 0.41 | 24.49 | 1.10 | 16.16 |
| | | 17.67 | 11.39 | | | | |
| | | 17.92 | 11.64 | | | | |
| 0 | B | 5.59 | | 9.65 | 214.00 | 13.14 | |
| | | 5.91 | | 10.78 | 224.30 | 14.27 | |
| | | 6.23 | | 10.67 | 289.60 | 16.11 | |
| 100 | B | 5.97 | 0.01 | 5.18 | 129.60 | 7.48 | 7.02 |
| | | 6.46 | 0.49 | | | | |
| | | 6.83 | 0.87 | | | | |
| 200 | B | 7.91 | 1.89 | 2.32 | 66.51 | 3.61 | 10.89 |
| | | 8.10 | 2.08 | | | | |
| | | 8.12 | 2.09 | | | | |
| 300 | B | 7.89 | 1.81 | 1.75 | 55.59 | 2.90 | 11.60 |
| | | 8.59 | 2.51 | | | | |
| | | 8.96 | 2.88 | | | | |
| 400 | B | 11.68 | 5.56 | 1.07 | 45.21 | 2.17 | 12.33 |
| | | 12.24 | 6.11 | | | | |
| | | 12.35 | 6.23 | | | | |
| 500 | B | 16.11 | 9.93 | 1.02 | 41.75 | 2.02 | 12.48 |
| | | 16.88 | 10.70 | | | | |
| | | 17.11 | 10.93 | | | | |
| 0 | C | 4.63 | | 4.64 | 229.20 | 10.62 | |
| | | 4.77 | | | | | |
| | | 4.90 | | | | | |
| 100 | C | 6.31 | 1.49 | 4.61 | 262.30 | 11.86 | (1.24) |
| | | 6.37 | 1.55 | | | | |
| 300 | C | 6.92 | 1.99 | 3.58 | 187.80 | 8.61 | 2.01 |
| | | 7.08 | 2.15 | | | | |
| 500 | C | 7.67 | 2.64 | 2.95 | 183.50 | 8.20 | 2.42 |
| | | 7.94 | 2.91 | | | | |
| 0 | D | 5.01 | | 9.57 | 281.80 | 15.15 | |
| 100 | D | 10.31 | 5.25 | 3.69 | 87.44 | 5.19 | 9.96 |
| | | 10.37 | 5.30 | | | | |
| 200 | D | 19.03 | 13.91 | 1.62 | 41.50 | 2.37 | 12.78 |
| | | 19.14 | 14.02 | | | | |
| 300 | D | 27.31 | 22.13 | 1.31 | 29.81 | 1.81 | 13.34 |
| | | 27.47 | 22.30 | | | | |

The effect of the chemicals on the dry oils, A, B, and D, fell generally along a straight line to the origin (correlation coefficient, R, of 97%). The wet oil, C, was distinct in separating at a much faster rate (54 μm/s/SN vs, 24 μm/s/SN), in keeping with the larger size and greater density of water droplets over asphaltene aggregates. An overall composite "Separation Potential" (SP) could be constructed as the normalized distance from the zero separation, zero velocity origin.

This Separation Potential shown in Table 6 was plotted against the dielectric response of the same chemicals on the same crudes. This showed that, in general, the greater the dielectric constant becomes, the less separation that results, following closely to an inverse square relationship with a correlation coefficient, R, of 85%.

The differentials (changes in separation/dielectric) were plotted, showing a similar correlation, with a coefficient, R, of 74%. In this case, the decrease in Separation Potential (resistance to separation) generally increased with increasing dielectric constant, until it hit a maximum equal to the amount of separation arbitrarily forced by the conditions of the settling test (heptane dilution, gravitational/centrifugal force, tube length, test duration). At that point, the settling test stopped differentiating (unless the conditions are changed), whereas, advantageously, the dielectric constant, not being subject to any arbitrary settling conditions, could continue to increase, further differentiating the chemicals.

Finally, the various dielectric and separation parameters were compared to the actual ability to inhibit asphaltene deposition in real oil production, as shown in Table 7, below. For two different oils, the minimum effective dose of chemical needed to inhibit asphaltenes corresponded to a dielectric constant of about 20.5±0.9 (4.5%), or to a net increase in dielectric constant of 14.8±0.3 (2.4%), a criterion significantly more consistent than any based on forced precipitation settling tests.

TABLE 7

Dielectric and Separation Parameters at Minimum Effective Field Inhibition Dose

| Performance Parameter Minimum Effective Field Dose | | Oil A 500 | Oil D 250 | Avg. | % +/− |
|---|---|---|---|---|---|
| Dielectric Parameters | Dielectric Constant | 21.4 | 19.6 | 20.5 | 4.5% |
| | Net Increase in Dielectric Constant | 15.1 | 14.4 | 14.8 | 2.4% |

TABLE 7-continued

Dielectric and Separation Parameters at
Minimum Effective Field Inhibition Dose

| Performance Parameter Minimum Effective Field Dose | | Oil A 500 | Oil D 250 | Avg. | % +/− |
|---|---|---|---|---|---|
| Separation Parameters | Separability Number | 0.4 | 1.5 | 0.9 | 56.3% |
| | Sedimentation Velocity | 24.5 | 35.7 | 30.1 | 18.6% |
| | Separation Potential (normalized distance) | 1.1 | 2.1 | 1.6 | 31.0% |
| | Decrease in Separation Potential | 16.2 | 13.1 | 14.6 | 10.6% |

Further Exemplary Embodiments

In view of the description above, the disclosure further provides the following non-limiting exemplary embodiments. The features described in these embodiments can be combined together in any manner not inconsistent with the teachings above.

Embodiment 1. A method for determining a content of disaggregated asphaltene in an inhibited crude oil, comprising measuring the dielectric constant of a sample of the crude oil, the sample having a first concentration of an asphaltene inhibitor;

providing a first dielectric correction factor for the first concentration of the asphaltene inhibitor;

calculating, e.g., by a computing device, a first corrected dielectric constant of the sample having the first concentration, using the first dielectric correction factor; and determining the content of disaggregated asphaltene in the first crude oil sample, based on the first corrected dielectric constant.

Embodiment 2. A method according to Embodiment 1, wherein the crude oil comprises water.

Embodiment 3. A method according to Embodiment 1 or Embodiment 2, wherein the first concentration is within the range of about 50 ppm to about 500 ppm.

Embodiment 4. A method according to any of Embodiments 1-3, wherein the dielectric correction factor for the first concentration of the asphaltene inhibitor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent.

Embodiment 5. A method according to Embodiment 4, wherein the average is evenly weighted.

Embodiment 6. A method according to Embodiment 4 or Embodiment 5, wherein the aliphatic hydrocarbon solvent is heptane.

Embodiment 7. A method according to Embodiment 4 or Embodiment 5, wherein the aromatic hydrocarbon solvent is toluene.

Embodiment 8. A method according to any of Embodiments 1-7, wherein calculating the first corrected dielectric constant comprises subtracting the dielectric correction factor from the dielectric constant of the sample having the first concentration.

Embodiment 9. A method for determining an asphaltene inhibition capacity of an asphaltene inhibitor for a crude oil, comprising measuring the dielectric constant of a first sample of the crude oil, the first sample having a first concentration of an asphaltene inhibitor;

providing a first dielectric correction factor for the first concentration of the asphaltene inhibitor;

calculating, e.g., by a computing device, a first corrected dielectric constant of the first sample having the first concentration, using the first dielectric correction factor;

measuring the dielectric constant of a second sample of the crude oil, the second sample having a second concentration of the asphaltene inhibitor;

providing a second dielectric correction factor for the second concentration of the asphaltene inhibitor;

calculating, e.g., by the computing device, a second corrected dielectric constant of the sample having the second concentration, using the second dielectric correction factor; and determining the asphaltene inhibition capacity of the asphaltene inhibitor, based on the second corrected dielectric constant and the first corrected dielectric constant.

Embodiment 10. A method according to Embodiment 9, wherein the crude oil comprises water.

Embodiment 11. A method according to Embodiment 9 or Embodiment 10, wherein the first concentration is up to 500 ppm, e.g., 0 ppm or within the range of about 50 ppm to about 500 ppm.

Embodiment 12. A method according to Embodiment 9 or Embodiment 10, wherein the second concentration is within the range of about 500 ppm to about 2,000 ppm.

Embodiment 13. A method according to any of Embodiments 9-12, wherein the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent; and the second dielectric correction factor is a weighted average of the dielectric constant of an aliphatic hydrocarbon sample having the second concentration of the asphaltene inhibitor dissolved in an aliphatic hydrocarbon solvent and the dielectric constant of an aromatic hydrocarbon sample having the second concentration of the asphaltene inhibitor dissolved in an aromatic hydrocarbon solvent.

Embodiment 14. A method according to Embodiment 13, wherein the average is evenly weighted.

Embodiment 15. A method according to Embodiment 13 or Embodiment 14, wherein the aliphatic hydrocarbon solvent is heptane.

Embodiment 16. A method according to Embodiment 13 or Embodiment 14, wherein the aromatic hydrocarbon solvent is toluene.

Embodiment 17. A method according to any of Embodiments 9-16, wherein calculating the first corrected dielectric constant comprises subtracting the first dielectric correction factor from the dielectric constant of the sample having the first concentration; and calculating the second corrected dielectric constant comprises subtracting the second dielectric correction factor from the dielectric constant of the sample having the second concentration.

Embodiment 18. A method according to any of Embodiments 9-17, wherein determining the asphaltene inhibition capacity is based on the magnitude of the difference between the second corrected dielectric constant and the first corrected dielectric constant.

Embodiment 19. A method according to any of Embodiments 9-18, further comprising
- measuring the dielectric constant of a third sample of the crude oil, the third sample having a third concentration of the asphaltene inhibitor;
- providing a third dielectric correction factor for the third concentration of the asphaltene inhibitor; and
- calculating, e.g., by the computing device, a third corrected dielectric constant of the sample having the second concentration, using the second dielectric correction factor;

wherein determining the asphaltene inhibition capacity of the asphaltene inhibitor is further based on the third corrected dielectric constant.

Embodiment 20. A method according to Embodiment 19, wherein the third concentration is at least about 2,000 ppm.

Embodiment 21. A method according to Embodiment 19 or Embodiment 20, wherein determining the asphaltene inhibition capacity comprises fitting the first corrected dielectric constant, the second corrected dielectric constant, and the third corrected dielectric constant to a mathematical function (e.g., a linear function or a polynomial function such as a parabolic function).

Embodiment 22. A method for selecting one or more target asphaltene inhibitors for a crude oil, comprising
- providing a plurality of asphaltene inhibitors;
- for each inhibitor of the plurality, determining an asphaltene inhibition capacity for the crude oil according to any of Embodiments 9-21;
- selecting, from the plurality, inhibitors having an asphaltene inhibition capacity above a predetermined cutoff, to provide one or more target asphaltene inhibitors for the crude oil.

Embodiment 23. A method for determining an effective (e.g., a minimum effective) asphaltene inhibitor concentration for a crude oil, comprising
- measuring the dielectric constant of a first sample of the crude oil, the first sample having a first concentration of an asphaltene inhibitor;
- providing a first dielectric correction factor for the first concentration of the asphaltene inhibitor;
- calculating, e.g., by a computing device, a first corrected dielectric constant of the sample having the first concentration, using the first dielectric correction factor;
- measuring the dielectric constant of the crude oil sample, the sample having a second concentration of the asphaltene inhibitor;
- providing a second dielectric correction factor for the second concentration of the asphaltene inhibitor;
- calculating, e.g., by the computing device, a second corrected dielectric constant of the sample having the second concentration, using the second dielectric correction factor;
- calculating, e.g., by the computing device, based on the first corrected dielectric constant and the second corrected dielectric constant, an effective concentration (e.g., a minimum effective concentration) of the asphaltene inhibitor sufficient to provide a predetermined minimum corrected dielectric constant; or a predetermined minimum net increase in corrected dielectric constant.

Embodiment 24. A method according to Embodiment 23, wherein the crude oil comprises water.

Embodiment 25. A method according to Embodiment 23 or Embodiment 24, wherein the first concentration is up to 500 ppm, e.g., 0 ppm or within the range of about 50 ppm to about 500 ppm.

Embodiment 26. A method according to Embodiment 23 or Embodiment 24, wherein the second concentration is within the range of about 500 ppm to about 2,000 ppm.

Embodiment 27. A method according to any of Embodiments 23-26, wherein
- the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent; and
- the second dielectric correction factor is a weighted average of the dielectric constant of an aliphatic hydrocarbon sample having the second concentration of the asphaltene inhibitor dissolved in an aliphatic hydrocarbon solvent and the dielectric constant of an aromatic hydrocarbon sample having the second concentration of the asphaltene inhibitor dissolved in an aromatic hydrocarbon solvent.

Embodiment 28. A method according to Embodiment 27, wherein the average is evenly weighted.

Embodiment 29. A method according to Embodiment 27 or Embodiment 28, wherein the aliphatic hydrocarbon solvent is heptane.

Embodiment 30. A method according to Embodiment 27 or Embodiment 28, wherein the aromatic hydrocarbon solvent is toluene.

Embodiment 31. A method according to any of Embodiments 23-30, wherein
- calculating the first corrected dielectric constant comprises subtracting the first dielectric correction factor from the dielectric constant of the sample having the first concentration; and
- calculating, e.g., by the computing device, the second corrected dielectric constant comprises subtracting the second dielectric correction factor from the dielectric constant of the sample having the second concentration.

Embodiment 32. A method according to any of Embodiments 23-31, wherein the minimum corrected dielectric constant is at least about 10, at least about 11, at least about 12, at least about 13, or at least about 15.

Embodiment 33. A method according to any of Embodiments 23-31, wherein the minimum net increase in corrected dielectric constant is at least about 5, at least about 6, at least about 7, at least about 8, or at least about 9, at least about 10.

Embodiment 34. A method according to any of Embodiments 23-33, further comprising
- measuring the dielectric constant of a third sample of the crude oil, the sample having a third concentration of the asphaltene inhibitor;
- providing a third dielectric correction factor for the third concentration of the asphaltene inhibitor; and
- calculating, e.g., by the computing device, a third corrected dielectric constant of the sample having the second concentration, using the second dielectric correction factor;

wherein calculating the effective concentration (e.g., the minimum effective concentration) of the asphaltene inhibitor is further based on the third corrected dielectric constant.

Embodiment 35. A method according to Embodiment 34, wherein the third concentration is at least about 2,000 ppm.

Embodiment 36. A method for inhibiting a crude oil (e.g., from a crude oil matrix), comprising
- determining an effective (e.g., a minimum effective) asphaltene inhibitor concentration for the crude oil as described in any of Embodiments 23-35; and
- adding an amount of the asphaltene inhibitor to the crude oil (e.g., to the crude oil matrix) sufficient to provide an inhibitor concentration of at least the effective asphaltene inhibitor concentration (e.g., at least the minimum effective asphaltene inhibitor concentration).

Embodiment 37. A method for inhibiting a crude oil (e.g., in a crude oil matrix), comprising
- selecting one or more target asphaltene inhibitors for the crude oil matrix as described in Embodiment 22; and
- adding an amount of a target asphaltene inhibitor to the crude oil (e.g., to the crude oil matrix).

Embodiment 38. A method according to Embodiment 37, further comprising, before adding an amount of the target asphaltene inhibitor to the crude oil, determining an effective asphaltene inhibitor concentration (e.g., a minimum effective asphaltene inhibitor concentration) for the crude according to any of Embodiments 23-35; wherein the amount of the target asphaltene inhibitor added to the crude oil is sufficient to provide an inhibitor concentration of at least the effective asphaltene inhibitor concentration (e.g., at least the minimum effective asphaltene inhibitor concentration).

Embodiment 39. A method according to any of Embodiments 1-38, wherein measuring the dielectric constant comprises measuring with a capacitor, e.g., a cylindrical capacitor, for example in any manner as described in U.S. Patent Application Publication no. 2018/0024084.

Embodiment 40. A non-transitory computer-readable medium having stored thereon program instructions that when executed by a processor of a computing device, cause the computing device to perform a set of functions comprising:
- receiving a first dielectric constant of a first sample of a crude oil, the sample having a first concentration of an asphaltene inhibitor;
- calculating a first corrected dielectric constant of the first sample having the first concentration, using a first dielectric correction factor;
- receiving a second dielectric constant of a second sample of the crude oil, the second sample having a second concentration of the asphaltene inhibitor;
- calculating a second corrected dielectric constant of the sample having the second concentration, using a second dielectric correction factor.

Embodiment 41. The medium of Embodiment 40, wherein the receiving of the first and/or second dielectric constant of a crude oil sample is from a dielectric constant measuring device, for example any device as described in U.S. Patent Application Publication no. 2018/0024084.

Embodiment 42. The medium of Embodiment 40 or Embodiment 41, wherein the set of functions further comprises, before calculating the first corrected dielectric constant,
- receiving a dielectric constant of an aliphatic hydrocarbon sample having the first concentration of the asphaltene inhibitor dissolved in an aliphatic hydrocarbon solvent;
- receiving a dielectric constant of an aromatic hydrocarbon sample having the first concentration of the asphaltene inhibitor dissolved in an aromatic hydrocarbon solvent; and
- calculating the first dielectric constant correction factor, using the dielectric constant of the aliphatic hydrocarbon sample having the first concentration and the dielectric constant of the aromatic hydrocarbon sample having the first concentration.

Embodiment 43. The medium of Embodiment 42, wherein the receiving of the dielectric constant of the aliphatic hydrocarbon sample and/or the aromatic hydrocarbon sample is from a dielectric constant measuring device.

Embodiment 44. The medium of Embodiment 40 or Embodiment 41, wherein the set of functions further comprises, before calculating the second corrected dielectric constant,
- receiving a dielectric constant of an aliphatic hydrocarbon sample having the second concentration of the asphaltene inhibitor;
- receiving a dielectric constant of an aromatic hydrocarbon sample having the second concentration of the asphaltene inhibitor; and
- calculating the second dielectric constant correction factor, using the dielectric constant of the aliphatic hydrocarbon sample having the second concentration and the dielectric constant of the aromatic hydrocarbon sample having the second concentration.

Embodiment 45. The medium of Embodiment 44, wherein the receiving of the dielectric constant of the aliphatic hydrocarbon sample and/or the aromatic hydrocarbon sample is from a dielectric constant measuring device.

Embodiment 46. The medium of any of Embodiments 40-45, wherein the set of functions further comprises calculating a first magnitude of the difference between the second corrected dielectric constant and the first corrected dielectric constant and determining an asphaltene inhibition capacity of the asphaltene inhibitor, based on the first magnitude.

Embodiment 47. The medium of any of Embodiments 40-46, wherein the set of functions further comprises
- receiving a third dielectric constant of the crude oil sample, the sample having a third concentration, using a third dielectric correction factor; and
- calculating a third corrected dielectric constant of the sample having the second concentration, using a third dielectric correction factor.

Embodiment 48. The medium of Embodiment 47, wherein the set of functions further comprises, before calculating the third corrected dielectric constant,
- receiving a dielectric constant of an aliphatic hydrocarbon sample having the third concentration of the asphaltene inhibitor;
- receiving a dielectric constant of an aromatic hydrocarbon sample having the third concentration of the asphaltene inhibitor; and
- calculating the third dielectric constant correction factor, using the dielectric constant of the aliphatic hydrocarbon sample having the third concentration and the dielectric constant of the aromatic hydrocarbon sample having the third concentration.

Embodiment 49. The medium of Embodiment 48, wherein the receiving of the dielectric constant of the aliphatic hydrocarbon sample and/or the aromatic hydrocarbon sample is from a dielectric constant measuring device.

Embodiment 50. The medium any of Embodiments 47-49, wherein the set of functions further comprises calculating a trend using the first magnitude and the second magnitude; and determining an asphaltene inhibition capacity of the asphaltene inhibitor, based on the trend.

The invention claimed is:

1. A method for determining a content of disaggregated asphaltene in an inhibited crude oil, comprising
measuring the dielectric constant of a sample of the crude oil, the sample having a first concentration of an asphaltene inhibitor;
providing a first dielectric correction factor for the first concentration of the asphaltene inhibitor;
calculating, by a computing device, a first corrected dielectric constant of the sample having the first concentration, using the first dielectric correction factor; and
determining the content of disaggregated asphaltene in the first crude oil sample, based on the first corrected dielectric constant.

2. The method according to claim 1, wherein the crude oil comprises water.

3. The method according to claim 1, wherein the first concentration is within the range of about 50 ppm to about 500 ppm.

4. The method according to claim 1, wherein the dielectric correction factor for the first concentration of the asphaltene inhibitor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent.

5. The method according to claim 4, wherein the aliphatic hydrocarbon solvent is heptane.

6. The method according to claim 4, wherein the aromatic hydrocarbon solvent is toluene.

7. The method according to claim 1, wherein calculating the first corrected dielectric constant comprises subtracting the dielectric correction factor from the dielectric constant of the sample having the first concentration.

8. A method for determining an asphaltene inhibition capacity of an asphaltene inhibitor for a crude oil, comprising
measuring the dielectric constant of a first sample of the crude oil, the first sample having a first concentration of an asphaltene inhibitor;
providing a first dielectric correction factor for the first concentration of the asphaltene inhibitor;
calculating, by a computing device, a first corrected dielectric constant of the first sample having the first concentration, using the first dielectric correction factor;
measuring the dielectric constant of a second sample of the crude oil, the second sample having a second concentration of the asphaltene inhibitor;
providing a second dielectric correction factor for the second concentration of the asphaltene inhibitor;
calculating, by the computing device, a second corrected dielectric constant of the sample having the second concentration, using the second dielectric correction factor; and
determining the asphaltene inhibition capacity of the asphaltene inhibitor, based on the second corrected dielectric constant and the first corrected dielectric constant.

9. The method according to claim 8, wherein
the first dielectric correction factor is a weighted average of the dielectric constant of an aliphatic hydrocarbon sample having the first concentration of the asphaltene inhibitor dissolved in an aliphatic hydrocarbon solvent and the dielectric constant of an aromatic hydrocarbon sample having the first concentration of the asphaltene inhibitor dissolved in an aromatic hydrocarbon solvent; and
the second dielectric correction factor is a weighted average of the dielectric constant of an aliphatic hydrocarbon sample having the second concentration of the asphaltene inhibitor dissolved in an aliphatic hydrocarbon solvent and the dielectric constant of an aromatic hydrocarbon sample having the second concentration of the asphaltene inhibitor dissolved in an aromatic hydrocarbon solvent.

10. The method according to claim 8, further comprising
measuring the dielectric constant of a third sample of the crude oil, the third sample having a third concentration of the asphaltene inhibitor;
providing a third dielectric correction factor for the third concentration of the asphaltene inhibitor; and
calculating, by the computing device, a third corrected dielectric constant of the sample having the second concentration, using the second dielectric correction factor;
wherein determining the asphaltene inhibition capacity of the asphaltene inhibitor is further based on the third corrected dielectric constant.

11. The method according to claim 10, wherein determining the asphaltene inhibition capacity comprises fitting the first corrected dielectric constant, the second corrected dielectric constant, and the third corrected dielectric constant to a mathematical function.

12. A method for selecting one or more target asphaltene inhibitors for a crude oil, comprising
providing a plurality of asphaltene inhibitors;
for each inhibitor of the plurality, determining an asphaltene inhibition capacity for the crude oil according to claim 8;
selecting, from the plurality, inhibitors having an asphaltene inhibition capacity above a predetermined cutoff, to provide one or more target asphaltene inhibitors for the crude oil.

13. A method for determining an effective (e.g., a minimum effective) asphaltene inhibitor concentration for a crude oil, comprising
measuring the dielectric constant of a first sample of the crude oil, the first sample having a first concentration of an asphaltene inhibitor;
providing a first dielectric correction factor for the first concentration of the asphaltene inhibitor;
calculating, by a computing device, a first corrected dielectric constant of the sample having the first concentration, using the first dielectric correction factor;
measuring the dielectric constant of the crude oil sample, the sample having a second concentration of the asphaltene inhibitor;
providing a second dielectric correction factor for the second concentration of the asphaltene inhibitor;
calculating, by the computing device, a second corrected dielectric constant of the sample having the second concentration, using the second dielectric correction factor;
calculating, by the computing device, based on the first corrected dielectric constant and the second corrected dielectric constant, an effective concentration of the asphaltene inhibitor sufficient to provide
- a predetermined minimum corrected dielectric constant; or
- a predetermined minimum net increase in corrected dielectric constant.

14. The method according to claim 13, wherein the minimum corrected dielectric constant is at least about 10.

15. The method according to claim 13, wherein the minimum net increase in corrected dielectric constant is at least about 5.

16. The method according to claim 13, further comprising
measuring the dielectric constant of a third sample of the crude oil, the sample having a third concentration of the asphaltene inhibitor;
providing a third dielectric correction factor for the third concentration of the asphaltene inhibitor; and
calculating, by the computing device, a third corrected dielectric constant of the sample having the second concentration, using the second dielectric correction factor;
wherein calculating the effective concentration of the asphaltene inhibitor is further based on the third corrected dielectric constant.

17. A method for inhibiting a crude oil comprising
determining an effective asphaltene inhibitor concentration for the crude oil as described in claim 13; and
adding an amount of the asphaltene inhibitor to the crude oil sufficient to provide an inhibitor concentration of at least the effective asphaltene inhibitor concentration.

18. A method for inhibiting a crude oil, comprising
selecting one or more target asphaltene inhibitors for the crude oil matrix as recited in claim 12; and
adding an amount of a target asphaltene inhibitor to the crude oil.

19. The method according to claim 18, further comprising
before adding an amount of the target asphaltene inhibitor to the crude oil, determining an effective asphaltene inhibitor concentration for the crude oil;
wherein the amount of the target asphaltene inhibitor added to the crude oil is sufficient to provide an inhibitor concentration of at least the effective asphaltene inhibitor concentration.

20. A non-transitory computer-readable medium having stored thereon program instructions that when executed by a processor of a computing device, cause the computing device to perform a set of functions comprising:
receiving a first dielectric constant of a first sample of a crude oil, the sample having a first concentration of an asphaltene inhibitor;
calculating a first corrected dielectric constant of the first sample having the first concentration, using a first dielectric correction factor;
receiving a second dielectric constant of a second sample of the crude oil, the second sample having a second concentration of the asphaltene inhibitor; and
calculating a second corrected dielectric constant of the sample having the second concentration, using a second dielectric correction factor.

* * * * *